(12) United States Patent
Asher et al.

(10) Patent No.: US 10,066,213 B2
(45) Date of Patent: Sep. 4, 2018

(54) USE OF CENTRIFUGATION-AIDED INFECTION TO INCREASE VIRUS TITER

(71) Applicant: EMD Millipore Corporation, Burlington, MA (US)

(72) Inventors: Damon Asher, Jefferson, MA (US); Anne Leahy, Medford, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 14/382,769

(22) PCT Filed: Mar. 13, 2013

(86) PCT No.: PCT/US2013/030880
§ 371 (c)(1),
(2) Date: Sep. 4, 2014

(87) PCT Pub. No.: WO2013/138465
PCT Pub. Date: Sep. 19, 2013

(65) Prior Publication Data
US 2015/0166965 A1    Jun. 18, 2015

Related U.S. Application Data

(60) Provisional application No. 61/610,220, filed on Mar. 13, 2012.

(51) Int. Cl.
| | | |
|---|---|---|
| *C12N 15/867* | (2006.01) | |
| *A61K 48/00* | (2006.01) | |
| *C07K 14/005* | (2006.01) | |
| *C12Q 1/68* | (2018.01) | |
| *A61K 39/00* | (2006.01) | |
| *C12N 7/00* | (2006.01) | |

(52) U.S. Cl.
CPC ...... *C12N 7/00* (2013.01); *C12N 2740/13051* (2013.01)

(58) Field of Classification Search
CPC .. A61K 2300/00; A61K 31/12; A61K 31/136; A61K 31/343; C07K 14/765
See application file for complete search history.

(56) References Cited

U.S. PATENT DOCUMENTS

| 5,834,256 A | * | 11/1998 | Finer ............... C07K 14/005 |
| | | | 435/320.1 |
| 6,214,982 B1 | | 4/2001 | Pasloske et al. |
| 2008/0206812 A1 | | 8/2008 | Atkinson et al. |

FOREIGN PATENT DOCUMENTS

| EP | 2377927 A1 | | 10/2011 |
| WO | 2005/047497 A1 | | 5/2005 |
| WO | 2007/135125 A1 | | 11/2007 |
| WO | WO2007135125 | * | 11/2007 |
| WO | WO2008001353 | * | 1/2008 |
| WO | 2008/127429 A2 | | 10/2008 |
| WO | 2011/130119 A2 | | 10/2011 |
| WO | WO2011130119 | * | 10/2011 |

OTHER PUBLICATIONS

Burns et al., "Vesicular stomatitis virus G glycoprotein pseudotyped retroviral vectors: concentration to very high titer and efficient gene transfer into mammalian and nonmammalian cells", 1993, Proc. Natl. Acad. Sci., 90:8033-8037.*
O'Doherty et al., "Human Immunodeficiency virus type 1 spinoculation enhances infection through virus binding", Journal of Virology, 2000, 74(21):10074-10080.*
Andreadis et al., "Toward a More Accurate Quantitation of the Activity of Recombinant Retroviruses: Alternatives to Titer and Multiplicity of Infection", Journal of Virology, vol. 74, No. 3, Feb. 2000, 9 pages.
Cornetta et al., "Retroviral Vector Production in the National Gene Vector Laboratory at Indiana University", Gene Therapy, vol. 12, 2005, pp. s28-s35.
Jewell et al., "Construction and Characterization of Deltaretrovirus Indicator Cell Lines", Journal of Virological Methods, vol. 123, No. 1, Jan. 2005, pp. 17-24.
Paul et al., "Increased Viral Titer Through Concentration of Viral Harvests from Retroviral Packaging Lines", Human Gene Therapy, vol. 4, No. 5, Oct. 1993, pp. 609-615.
Platt et al., "Rapid Dissociation of HIV-1 from Cultured Cells Severely Limits Infectivity Assays, Causes the Inactivation Ascribed to Entry Inhibitors, and Masks the Inherently High Level of Infectivity of Virions", Journal of Virology, vol. 84, No. 6, Mar. 2010, pp. 3106-3110.
Tenser et al., "Mechanisms of Herpes Simplex Virus Infectivity Enhanced by Ultracentrifugal Inoculation", Infection and Immunity, vol. 30, No. 1, Oct. 1980, pp. 193-197.
Thomas et al., "Efficiency of Human Immunodeficiency Virus Type 1 Postentry Infection Processes: Evidence against Disproportionate Numbers of Defective Virions", American Society for Microbiology, Journal of Virology, vol. 81, No. 8, Apr. 2007, pp. 4367-4370.
International Search Report and Written Opinion received for PCT Patent Application No. PCT/US2013/030880, dated Jul. 23, 2013, 10 pages.
International Preliminary Report on Patentability received for PCT Patent Application No. PCT/US2013/030880, dated Sep. 25, 2014, 6 pages.
Bahnson et al., "Centrifugal Enhancement of Retroviral Mediated Gene Transfer", Journal of Virological Methods, vol. 54, 1995, pp. 131-143.

(Continued)

*Primary Examiner* — Barry A Chestnut
(74) *Attorney, Agent, or Firm* — EMD Millipore Corporation

(57) ABSTRACT

The invention relates to a process for increasing the observed titer of a virus stock for the purpose of increasing the calculated log reduction (LRV) in virus clearance studies. A tissue culture or assay plate is seeded with an indicator cell line and titrated with a virus stock followed, by a centrifugation step for about 5 minutes to about 24 hours at a g-force ranging from about 50×g to about 2400×g, and at a temperature from about 4° C. to about 39° C. The resulting calculated virus titer after undergoing the centrifugation step is 10-fold higher than the virus titer would be if determined in the absence of the centrifuging step.

11 Claims, 1 Drawing Sheet

(56) References Cited

OTHER PUBLICATIONS

Burns et al., "Vesicular Stomatitis Virus G Glycoprotein Pseudotyped Retroviral Vectors: Concentration to Very High Titer and Efficient Gene Transfer into Mammalian and Nonmammalian Cells", Proc. Natl. Acad. Sci. USA, vol. 90, Sep. 1993 ,pp. 8033-8037.

Celis, Julio E., "Cell Biology: A Laboratory Handbook", Academic Press, Inc., vol. 1, 1994, pp. 5-17 & 25-42.

Forestell et al., "Improved Detection of Replication-Competent Retrovirus", Journal of Virological Methods, vol. 60, 1996, pp. 171-178.

Rebel et al., "One-Day Ex Vivo Culture Allows Effective Gene Transfer into Human Nonobese Diabetic/Severe Combined Immune-Deficient Repopulating Cells Using High-Titer Vesicular Stomatitis Virus G Protein Pseudotyped Retrovirus", Blood, vol. 93, No. 7, Apr. 1, 1999, pp. 2217-2224.

Yee et al., "A General Method for the Generation of High-Titer, Pantropic Retroviral Vectors: Highly Efficient Infection of Primary Hepatocytes", Proc. Natl. Acad. Sci. USA, vol. 91, No. 8, Sep. 1994, pp. 9564-9568.

Extended European Search Report received for European Patent Application No. 13761659.5, dated Jul. 28, 2015, 7 pages.

Guo et al., "Spinoculation Triggers Dynamic Actin and Cofilin Activity That Facilitates HIV-1 Infection of Transformed and Resting CD4 T Cells", Journal of Virology, vol. 85, No. 19, Oct. 2011, pp. 9824-9833.

Hodgkin et al., "Murine Cytomegalovirus Binds Reversibly to Mouse Embryo Fibroblasts: Implications for Quantitation and Explanation of Centrifugal Enhancement", Journal of Virological Methods, vol. 22, 1988, pp. 215-230.

Kwon et al., "Determination of Infectious Retrovirus Concentration from Colony-Forming Assey Quantitative Analysis", Journal of Virology, vol. 77, No. 10, May 2003, pp. 5712-5720.

O'Doherty et al., "Human Immunodeficiency Virus Type 1 Spinoculation Enhances Infection through Virus Binding", Journal of Virology, vol. 74, No. 21, Nov. 2000, pp. 10074-10080.

Tianyahaijiao, "Effects of the Quality of a Virus Solution on Validation of Virus Clearance Filter Membrane", Blog of Tianyahaijiao, Oct. 13, 2011.

Ye et al., "Centrifugal Enhancement of Hepatitis C Virus Infection of Human Hepatocytes", J Virol Methods, vol. 148, No. 1-2, Mar. 2008, pp. 161-165.

"Basic Requirements for Viral Safety of Biotechnological/Biological Products listed in Japanese Pharmacopoeia", The Japanese Pharmacopoeia, Supplement I of the 14th edition, Dec. 27, 2002, pp. 2166-2194.

Damico et al., "Soluble Receptor-Induced Retroviral Infection of Receptor-Deficient Cells", Journal of Virology, vol. 74, No. 14, Jul. 2000, pp. 6469-6475.

Ishizaki, Ryotaro, "Survey of Murine Leukemia Among Experimental Mice: COMUL Test with Rabbit Immune Serum", Journal of the Japan Veterinary Medical Association, vol. 34, No. 11, 1981, pp. 538-542.

Li et al., "PG-4 Cell Plaque Assay for Xenotropic Murine Leukemia Virus", Journal of Virological Methods, vol. 81, Issues 1-2, Aug. 1999, pp. 47-53.

\* cited by examiner

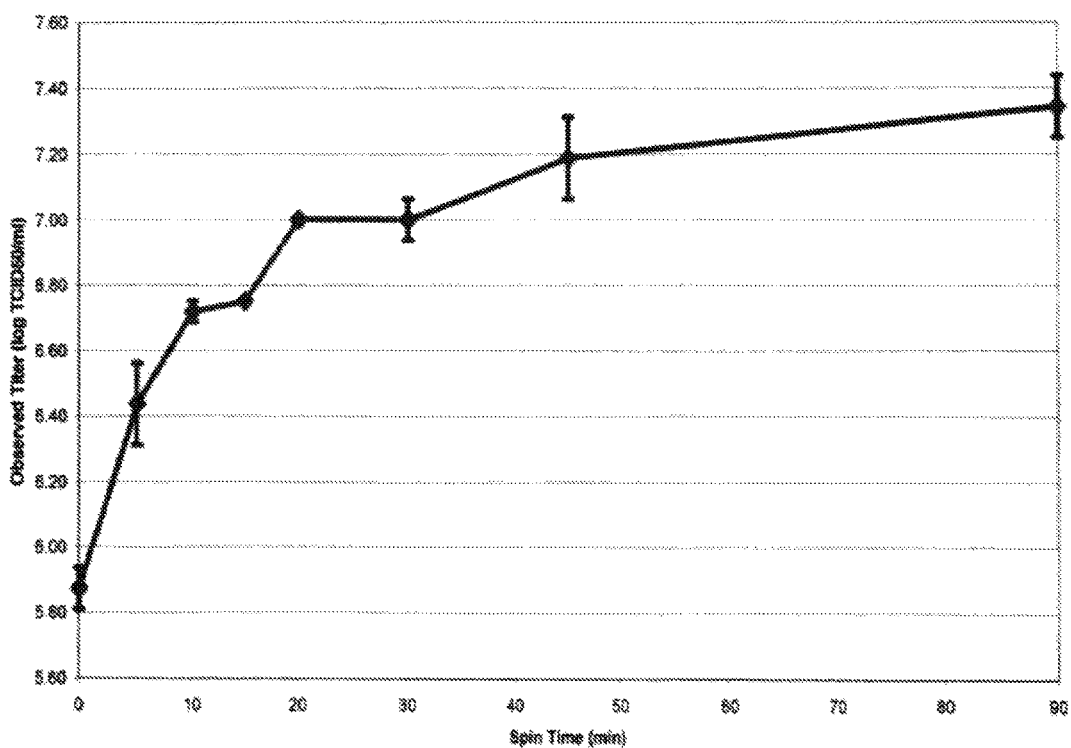

USE OF CENTRIFUGATION-AIDED INFECTION TO INCREASE VIRUS TITER

RELATED APPLICATIONS

The present application claims the benefit of priority of U.S. Provisional Patent Application No. 61/610,220, filing date Mar. 13, 2012, which is incorporated by reference herein in its entirety.

DESCRIPTION OF THE INVENTION

Field of the Invention

This invention relates to increasing the sensitivity of virus titer assay resulting in an increase in the calculated titer of a virus stock. More particularly, it relates to the use of centrifugation-aided infection procedure to increase contact between a virus or virus-like particle and an indicator cell monolayer, for the purpose of maximizing infection probability, thus increasing the measured virus titer. This increased virus titer can be beneficial in the calculated log reduction valve (LRV) in virus clearance studies.

Background of the Invention

Biopharmaceutical products, such as monoclonal antibodies, recombinant proteins, vaccines, blood derivatives and animal products carry a risk of transmitting infectious viruses. This is due to source material possibly being intrinsically contaminated with viruses or virus-like particles. Additionally, manufacturing processes of biopharmaceutical products are susceptible to virus contamination from extrinsic sources. As a result, manufacturers of biopharmaceutical products are required to incorporate sufficient virus clearance steps into their manufacturing processes to ensure that their products are contaminant virus-free. Such virus clearance steps typically involve virus removal steps, virus inactivation steps or a combination of these steps. It is a safety and regulatory imperative that manufacturing processes of biopharmaceutical products incorporate these virus clearance steps.

Evaluation of virus clearance step effectiveness in the manufacturing process is necessary. The purpose of virus clearance evaluation is to assess the capability of a manufacturing production process to inactivate and/or remove potential virus contaminants. Spiking studies are typically used to evaluate and validate virus clearance steps in a scaled down model of a production-scale process.

Spiking studies are performed by adding virus to (or "spiking") biopharmaceutical process intermediate material. The material (or "feed") is then taken through a miniaturized version of a manufacturing process step (or "unit operation"). The amount of virus in the feed before and after the unit operation is quantified, and the difference defines the virus reduction of the step. The virus reduction is typically expressed in terms of $\log_{10}$ reduction value (LRV), This type of study is called "virus clearance," "virus reduction", or "virus validation."

Regulatory expectations for biopharmaceutical products are that manufacturing processes provide an adequate total LRV for various model viruses to ensure that significant quantities of a viral contaminant are not likely to reach the final product. The total LRV for a process is obtained by performing scaled down viral clearance studies for each relevant process step. The LRVs obtained for each step are then added together to obtain the total LRV for the process. Only unit operation LRVs that are "orthogonal" may be added together in this way, meaning that each step that makes up the LRV sum must eliminate virus by a different mechanism.

The virus assays most commonly used to quantify virus contaminants in virus clearance studies are tissue culture limiting dose 50% ($TCID_{50}$), plaque-forming unit (PFU), and focus-forming unit (FFU) assays. Each of these assays operates by exposing dilutions of the material to be tested to suitable cells in culture. After a sufficient amount of time, the cells are then inspected for signs of virus infection, usually by microscope. The number of infectious events detected at each dilution is then used to calculate the virus titer.

Some unit operations are highly effective for virus clearance and reduce virus to the point where no virus is detected in the post-step material. In these cases, the virus titer in the post-step material is assumed to be less than or equal to the limit of detection for the virus assay. The limit of detection is dependent upon the amount of material assayed; screening of greater sample volumes lowers the limit of detection. Assuming no virus is detected in post step material, the LRV determined for the operation ultimately depends on only two factors: the amount of material surveyed/assayed for the presence of virus (which determines the limit of detection), and the titer of virus in the spiked feed material.

The maximum virus titer obtainable in spiked feed is limited by the titer of the virus stock. Regulatory guidelines specify that feed materials should not be spiked with a volume of virus stock higher than 10% of the combined volume. Moreover, practical considerations of the impact of the virus spike on the performance of the unit operation often limit the percentage of virus spike to a lower value. In any case, higher titer virus stocks enable higher titer spiking of feed material. This in turn means that higher titer virus stocks enable the demonstration of higher LRVs for a highly effective virus clearance steps.

For example, assume the limit of detection of the virus assay when 10 mL of sample is surveyed is 0.5 $\log_{10}TCID_{50}$/mL. Also assume that the unit operation to be tested is a filtration step, with no change in volume of the material across the step. The feed material may only be spiked with a maximum of 1% virus stock due to limitations of the filter. If the titer of the virus stock is 7.0 $\log_{10}TCID_{50}$/mL, the titer in the 1% spiked feed material would be 5.0 $\log_{10}TCID_{50}$/mL. If the unit operation resulted in the detection of no virus in the post-step material, the LRV reported would be "≥4.5" (5.0-0.5). However, If the virus stock available had a measured titer of 8.0 $\log_{10}TCID_{50}$/mL, the reported LRV would be "≥5.5", indicating measured evidence of a 10-fold greater ability of that step to remove virus.

The ability to maximize the reported LRV of unit operations is of great economic value to biopharmaceutical manufacturers. Particularly in the case of retroviruses, specific targets for total. LRV across the manufacturing process must be obtained in order to meet regulatory expectations. If the unit operations present in a process cannot meet the LRV target, then, additional manufacturing steps must be added to improve the total LRV claim.

Additionally, virus clearance validation is an expensive process, so it is desirable to minimize the number of steps that must be validated. Therefore, virus stocks of higher observed measured titer can enable higher LRVs to be obtained for each unit operation, facilitating achievement of targets using a minimum of process steps, thereby resulting in significant cost savings.

The assays used to determine' infectious virus titer are typically inefficient in that they do not detect every infectious virus particle present in the material. The efficiency of these assays is affected by a number of factors including the cell lines used, media additives, and environmental conditions. It is apparent that biopharmaceutical manufacturers need an economical technique to increase the efficiency of virus assays, and thus. Increase the measured titer of a virus sample while in turn minimizing the added complexity and the number of steps that must be validated. An increase in the observed measured titer of a virus sample is of great benefit for virus clearance studies because this can increase the LRVs that can be demonstrated for highly effective virus clearance operations.

SUMMARY OF THE INVENTION

An object of the present invention is to provide a process for increasing the observed titer of a virus stock for the purpose of increasing the calculated log reduction (LRV) in virus clearance studies. This process uses centrifugation-aided infection (or "spinoculation") of indicator cells in virus cell culture plates to improve the detection of titrated virus in infectivity-based assays such as $TCID_{50}$, plaque-forming unit (PFU), and focus-forming unit (FFU) assays.

Another object of the present invention is to provide a process for increasing the observed titer of a virus stock for the purpose of increasing the calculated log reduction (LRV) in virus clearance studies by centrifuging (i.e., spinoculating) an assay plate having a cell culture media, an indicator cell line, and a virus stock located thereon, wherein the resulting calculated virus titer is approximately 10-fold higher than a resulting virus titer calculated in the absence of the centrifugation (i.e., spinoculation) step.

In still other embodiments, the invention is directed towards the centrifugation of tissue culture plates to improve the detection of a retrovirus in $TCID_{50}$ assays, using spinoculation to increase the observed titer of a virus stock for the ptirpose of increasing the calculated log reduction (LRV) in virus clearance studies. Spinoculation is used to increase the efficiency of cell infection of virus at low titers, so that infections take place at dilutions of virus samples where they otherwise would most likely not. This results in virus stocks designated as having a higher calculated virus titer values than they would otherwise, and thus virus spikes of higher titer can be used in virus clearance. Because virus clearance steps often reduce virus to the point where the virus can no longer be detected, this higher spike results in a higher calculated LRV.

Additional features and advantages of the invention will be set forth in the detailed description and claims, which follows. Many modifications and Variations of this invention can be made without departing from its spirit and scope, as will be apparent to those skilled in the art. It is to be understood that the foregoing general description and the following detailed description, the claims, as well as the appended drawings are exemplary and explanatory only, and are intended to provide an explanation of various embodiments of the present teachings. The specific embodiments described herein are offered by way of example only and are not meant to be limiting in any way.

BRIEF DESCRIPTION OF THE DRAWINGS

FIG. 1 is a graphical representation of the measured virus titer vs. centrifugation time.

DETAILED DESCRIPTION OF THE EMBODIMENTS

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the Invention are approximations, the numerical values set forth in the specific examples are reported as precisely as possible.

Moreover, all ranges disclosed herein are to be understood to encompass all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Before describing the present invention in further detail, a number of terms will be defined. Use of these terms does not limit the scope of the invention but only serves to facilitate the description of the invention.

As used herein, the singular forms "a," "an," and "the" include plural referents unless the context clearly dictates otherwise.

The practice of the present invention will employ, unless otherwise indicated, conventional techniques of cell biology, molecular biology, cell culture, virology, immunology and the like which are in the skill of one in the art. These techniques are fully disclosed in current literature and reference in made specifically to Sambrook, Fritsch and Maniatis eds., "Molecular Cloning, A Laboratory Manual", ed Ed., Cold Spring Harbor Laboratory Press (1989); Cells J. E. "Cell Biology. A Laboratory Handbook" Academic Press, Inc. (1994) and Bahnson et at, J. of Virol. Methods 54:131-143 (1995).

All publications and patent applications cited in this specification are indicative of the level of skill of those skilled in the art to, which this invention pertains and are hereby incorporated by reference in their entirety.

Contamination of biopharmaceutical products, e.g., antibodies, recombinant proteins, vaccines, blood derivatives, plasma, and animal products, etc., by bacteria, viruses, prions, and the like, is a serious risk that needs to be sufficiently addressed. Contamination can arise by different ways. For example, it can occur because the source material (e.g., the cells in a cell culture, the blood product, etc.) is intrinsically contaminated with viruses.

The manufacturing processes of biopharmaceutical products are also susceptible to virus contamination from extrinsic sources (e.g., inadvertent introduction from use of non-sterile or improperly sterilized materials). Because of the nature of the products, manufacturers of biopharmaceutical products are highly regulated and are required to incorporate sufficient virus clearance steps into their manufacturing processes to ensure that their products are contaminant-free. Multiple virus clearance steps can be incorporated into a manufacturing process. Each of these virus clearance steps needs to be evaluated for its effectiveness and thus, validated before a biopharmaceutical Manufacturing process is approved. Virus clearance steps typically involve either virus removal steps or virus inactivation steps.

"Virus removal" as used herein means a method in which the virus is physically removed from the sample. This is often achieved by either nanofiltration or chromatography. Nanofiltration techniques remove viruses by size exclusion. The success of chromatographic methods for removing viruses depends on the column composition and the reagents (e.g., buffers) used.

"Virus inactivation", as used herein means a method in which the viruses may remain in the final product, but in a non-infective (inactive) form. Many viruses contain lipid or protein coats that can be inactivated by chemical alteration. Alternatively, some viral inactivation processes denature the virus completely. Examples of virus inactivation methods include solvent and/or detergent inactivation, pasteurization (e.g., heating to high temperatures), pH inactivation (e.g., using an acidic pH), and irradiation (e.g., ultraviolet (UV) or gamma irradiation).

The concentration of a contaminating virus, or the risk of virus contamination, in a manufacturing process may be extremely low, but, because viruses are by their nature infective, even one viral particle can, be sufficient to ruin an entire run in a manufacturing process. It is for this reason that special measures must be taken to determine the appropriate removal or inactivation methods in a manufacturing process. As such, the effectiveness of such virus clearance methods needs to be evaluated and validated. Spiking studies were created specifically for this purpose.

Spiking studies use a scaled down model of the virus clearance step of a production-scale process to evaluating and/or validate the virus clearance steps and to evaluating and/or validate the apparatus used in the virus clearance method. Virus stocks of as high a titer as possible are desirable. This is due in part because the volume of virus spike that can be added to a test system is limited by Government Mandated Regulatory Guidelines (e.g., The U.S. Food and Drug Administration (FDA)).

The titer of the virus stock therefore determines the maximum possible concentration of virus spiked into the test material. As a result, the actual capacity of the test unit to clear virus in the production process may be underestimated. Current limitations of our knowledge of virus production has resulted in methods that lack the capacity to produce virus stocks of high purity and high titer.

The techniques provided herein increase the efficiency of virus titration assays, resulting in virus stocks having a measured virus titer about tenfold (10-fold) higher than the virus titer would be if measured in the absence of these techniques. This increase in measured virus titer is of great benefit for virus clearance studies because this can increase the LRVs that can be demonstrated for highly effective virus clearance operations.

The Tissue Culture Infectious Dose 50% ($TCID_{50}$) assay is a method for counting the number of infectious viral particles in a sample. The $TCID_{50}$ is the quantity of a pathogenic agent (virus) that will produce a cytopathic effect in 50% of the cultures inoculated. The $TCID_{50}$ value is proportional to, but not the same as, the number of infectious virions in a sample. Titers determined using this method are typically reported as $TCID_{50}$/ml.

When no virus at all is detected by the assay, a maximum possible titer for the sample is determined using a Minimal. Limit of Detection (LOD) calculation. This calculation considers the sensitivity of the assay and reports the most virus that could be in a sample without the assay detecting any. The result of these calculations is a titer reported as "≤X", meaning that the actual titer in the sample is X or lower (to a 95% certainty). This LOD calculation depends solely on the quantity of sample tested and any predilutions made to the sample before assaying.

Infectious virus titer is usually quantified by either plaque-forming unit (PFU) assay or tissue culture infectious dose 50% ($TCID_{50}$) assay. Both of these techniques involve adding serial, dilutions of a virus-containing solution to a tissue culture containing susceptible host cells. The amount of virus in the original sample is then calculated by counting the number of infection events on the cells. The amount of virus detected by these assays is limited by the ability of the virus to infect the host cells and the rate at which it does so.

The idea of increasing the infection of cells by retrovirus by centrifuging the cell culture is known, see for example, in Forstell, et al. (1996) J. Viral Meth 60:171. Forstell demonstrated that centrifugation during infection, or spinoculation, increased the ability of retrovirus to transduce a reporter gene into host cells.

As taught herein, and previously unbeknownst to us, we have found that the centrifugation of tissue culture or assay plates (i.e., a process referred to herein as spinoculation or centrifugal inoculation of cell cultures) appears to improve the detection of retrovirus in $TCID_{50}$ assay.

As taught herein, and previously unbeknownst to us, when Xenotropic twine leukemia viruses (X-MuLV) are titrated onto a tissue culture or assay plate seeded with an indicator cell line are centrifuged, that centrifugation or spinoculation step of the tissue culture plates after the virus has been added to the cell lines on the plate unexpectedly increases the sensitivity of the $TCID_{50}$ assay such, that the virus titer of the original stock is calculated to be approximately 10-fold higher than when the $TCID_{50}$ assay is performed by standard methods. Other than the addition of the centrifugation or spinoculation step, the $TCID_{50}$ assay is performed as a usual standard. $TCID_{50}$ assay known in the art.

The exact mechanism by which spinoculation works is unclear. The centrifugal force is insufficient, to sediment the virus onto the cells. While not wishing to be bound to any one theory, it is postulated that there may be some deformation of the cell surface that enables More efficient virus attachment. This could be especially effective for retrovirus because retrovirus is known to have a natural charge-based repulsion to the cell surface.

The use of spinoculation to increase the titer of a virus stock is a technique that, up until now has not been used in areas such as virus clearance studies. We have found that when a virus stock (i.e., X-MuLV stock) is titrated by standard $TCID_{50}$ methods, but with the addition of centrifugation (i.e., spinoculation) of the cell culture plates (e.g., at 1800 RPM) over increasing periods of times after addition of the virus, a gradual increase in the measured titer of the virus stock was unexpectedly discovered.

The measured titer of a virus stock is dependent upon the methods and/or processes used to determine that measurement. We have found that modifying a standard $TCID_{50}$ assay by the spinoculation process as taught herein provides an unexpectedly increased sensitivity to the titer of a virus stock, which has the benefit of effectively increasing the titers of existing virus stocks (e.g., X-MuLV) by 10-fold.

Increasing the titers of existing virus stocks 10-fold has a direct impact upon the log reduction values (LRV) achieved when using such virus stocks for its intended purpose in virus clearance validation studies. Use of the spinoculation technique as provided herein in virus clearance studies essentially provides an extra 1 LRV for retroviruses when the clearance operation being tested results in no virus being detected in the post-unit operation material. In such cases, the LRV for a virus clearance process is based entirely on the titer of virus in the spiked material and the amount of post-unit operation material tested. Because spinoculation increases the measured titer of virus of the spiked material by 1 log, this translates directly into a 1 LRV gain in clearance (vs. titration of the spiked feed by methods traditionally used).

Given that biopharmaceutical producers have hard targets that must be met for retrovirus clearance (typically a total of 12-20 LRV across the entire process), use of the spinoculation techniques as taught herein unexpectedly provides the ability to achieve an extra 1 LRV to virus filtration steps, which typically result in no virus being detected in the filtrate. In addition, the spinoculation technique taught herein can be used at every vim clearance step, and potentially add 1 LRV to each step that is effective enough to reduce virus to non-detectable levels. This could potentially add a total of 2 to 4 LRV for retrovirus to typical MAb processes.

The following examples are provided for the purpose of further illustrating the present invention but are in no way to be taken as limiting. In addition, the following examples are provided so as to provide those of ordinary skill in the art with a complete disclosure and description of how to make and how to practice the methods of the invention, and are not intended to limit the scope of what the inventor regards as his invention. Efforts have been made to insure accuracy with respect to numbers used (e.g. amounts, temperature, etc.), but some experimental errors and deviation should be accounted for. Unless indicated otherwise, temperature is in degree Celsius (AC), chemical reactions were performed at atmospheric pressure or transmembrane pressure, as indicated, the term "ambient temperature" refers to approximately 25° C. and "ambient pressure" refers to atmospheric pressure.

The invention will be further clarified by the following examples which are intended to be exemplary of the invention.

EXAMPLES

Example 1

Test materials used:
A) Xenotropic murine leukemia virus (X-MuLV)
  1) Strain: ATCC VR-1447
  2) Prep type: VSP X-MuLV Mk1 purified
  3) Lot # CP2; Production date: November 2009
  4) Recorded titer: 5.94 log $TCID_{50}$/ml
B) Minute virus of mice (MVM)
  1) Strain: ATCC VR-1346
  2) Prep type: VSP MVM Mk2.1
  3) Recorded titer 10.4 log $TCID_{50}$/ml
C) Plate preparation
  1) The day prior to the experiment, 96-well plates were seeded with PG-4 cells (labeled #1 to #16) by standard protocol (each well containing 100 µl media with 5.0 µg polybrene/ml (final concentration will be 2.54µg/ml after inoculation).
  2) Also, 96-well plates were seeded with 324K cells (labeled #17 to #20) by standard protocol.
D) Virus stock dilution
  1) A single ten-fold dilution series was made of the X-MuLV stock virus in 50 ml tubes ($10^{-2}$ through $10^{-8}$).
    (a) Label seven (7) tubes #2 through #8.
    (b) The following media was used for the dilutions:
      (1) McCoy's media supplemented with 1% FBS, 1× Penn/Strep, 1× L-Glut, 1× NEAA (as per standard X-MuLV titration protocol).
    (c) 49.5 ml of media was added to the #2 tube. 45 ml of media was added to tubes #3 through #8.
    (d) 0.5 ml virus stock was added to the #2 tube and mixed.
    (e) 5 ml was transferred from the #2 tube to the #3 tube, and mixed. A tenfold dilution series was continued to the #8 tube.
  2) A single ten-fold dilution series of the MVM stock virus was made in 50 ml tubes ($10^{-2}$ through $10^{-13}$).
    (a) Twelve (12) tubes were, labeled #2 through #13
    (b) The following media was used for the dilutions:
      (1) DMEM media supplemented with 1% FBS, 1× Penn/Strep, 1× L-Glut, 1× NEAA (as per standard MVM titration protocol).
    (c) 19.8 ml of media was added to the #2 tube. 18 ml media was added to tubes #3 through #7.
  3) 0.2 ml virus stock was added to the #2 tube and mixed.
  4) 2 ml was transferred from the #2 tube to the #3 tube and mixed. A tenfold dilution series was continued to the #13 tube,
E) Virus titration
  1) The X-MuLV and MVM were titrated by standard protocols using the dilutions made above.
    (a) X-MuLV: titrated across plates #1 to #16 from to $10^{-3}$ to $10^{-8}$
    (b) MVM: titrated across plates #17 to #20 from to $10^{-8}$ to $10^{-13}$
  2) AH plates were placed in a 37° C. at 5% $CO_2$ incubator until their turn in the centrifuge and after.
F) Spinoculation
  1) Plates were centrifuged for the times specified in Table 1, provided in section (e) below.
    (a) The 0 Min controls was simply left in the incubator.
    (b) Speed: 1800 RPM=670×g
    (c) Temperature: set to 25° C.
    (d) Each plate was spun continuously for the complete duration of its run (i.e., no start/stopping)
    (e)

TABLE 1

| Centrifugation time (min) | X-MuLV | MVM |
|---|---|---|
| 0 | 1-2 | 17-18 |
| 5 | 3-4 | |
| 10 | 5-6 | |
| 15 | 7-8 | |
| 20 | 9-10 | |
| 30 | 11-12 | |
| 45 | 13-14 | 19-20 |
| 90 | 15-16 | |

G) Plates were incubated at 37° C. at 5% $CO_2$ until appropriate read time (7 days for XMLV, 10 days for MVM), then the plates were scored.

H) Results provided in Tables 2 and 3

TABLE 2

Titers for XMLV (Xenotropic murine leukemia virus)

| Sample Name | Time (min) | Titer (log $TCID_{50}$) | Std Error | vs. time 0 |
|---|---|---|---|---|
| Control | 0 | 5.88 | ±0.06 | |
| 5 min Spin | 5 | 6.44 | ±0.13 | +0.56 |
| 10 min Spin | 10 | 6.72 | ±0.03 | +0.84 |
| 15 min Spin | 15 | 6.75 | ±0.00 | +0.88 |
| 20 min Spin | 20 | 7.00 | ±0.00 | +1.13 |
| 30 min Spin | 30 | 7.00 | ±0.06 | +1.13 |
| 45 min Spin | 45 | 7.19 | ±0.13 | +1.31 |
| 90 min Spin | 90 | 7.34 | ±0.09 | +1.47 |

TABLE 3

Titers for MVM (Minute virus of mice)

| Sample Name | Titer (log $TCID_{50}$) | Std Error |
|---|---|---|
| Control-MVM | 9.53 | ±0.22 |
| 45 min | 9.56 | ±0.06 |

Compared to the Control, an increase of about a 1.5 log in virus titer was seen after spinning the plates containing XMLV for 90 minutes in Table 2. There was no significant difference from the Control in the MVM plates in Table 3.

FIG. 1 is a graphical representation of the measured virus titer vs. centrifugation time. A X-MuLV stock was titrated by standard $TCID_{50}$ methods, with the addition of centrifugation of the 96-well plates at 1800 RPM for various times after addition of the virus. As the plates were spun over increasing time periods, a gradual increase in measured virus titer was seen, with the greatest increases occurring within the first 60 minutes.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and Whether broader, narrower, equal, or different in scope to the original claims, also are regarded as included within the subject matter of the inventions of the present disclosure.

What is claimed is:

1. A process for increasing the observed titer of a Xenotropic murine leukemia virus (X-MuLV) stock for the purpose of increasing the calculated log reduction (LRV) in a virus clearance study comprising the steps of:

a) providing a X-MuLV stock, cell culture media, indicator cell line, and an assay plate;

b) adding the indicator cell line and media to the assay plate;

c) adding the X-MuLV stock to the cell line and media on the assay plate;

d) centrifuging the assay plate containing the cell line, media, and X-MuLV stock;

e) stopping the centrifuging step;

f) incubating the assay plate centrifuged in step d); and g) measuring the observed titer of the X-MuLV stock, wherein the resulting titer of the X-MuLV stock is 10-fold higher than the X-MuLV titer would be if measured in the absence of the centrifuging step (d).

2. The process of claim 1, wherein the assay plate is selected from the group consisting of a tissue culture plate, a well plate, a flask or a test tube.

3. The process of claim 1, wherein centrifuging step (d) occurs from about 5 minutes to 24 hours at g-force range from about 50×g to 2400×g.

4. The process of claim 1, wherein centrifuging step (d) occurs from about 30 minutes to 120 minutes at g-force range from about 500×g to 1000×g.

5. The process of claim 1, wherein the temperature during centrifuging step (d) is about 4° C. to 39° C.

6. The process of claim 1, wherein the temperature during centrifuging step (d) is about 21° C. to 39° C.

7. The process of claim 1, further comprising an additional incubating step, wherein the assay plate containing X-MuLV stock, media and cell line is additionally incubated prior to the centrifuging step (d).

8. The process of claim 1, wherein the X-MuLV stock is prediluted.

9. The process of claim 1, wherein the incubation temperature is about 37° C.

10. The process of claim 7, wherein the incubation temperature is about 37° C.

11. The process of claim 1, wherein the temperature during centrifuging step (d) is about 25° C.

* * * * *